United States Patent
Ochs et al.

(10) Patent No.: US 9,357,953 B2
(45) Date of Patent: Jun. 7, 2016

(54) SYSTEM AND METHOD FOR DIAGNOSING SLEEP APNEA

(75) Inventors: James Ochs, Seattle, WA (US); Scott Amundson, Oakland, CA (US); Keith Batchelder, New York, NY (US); Paul Mannheimer, Danville, CA (US)

(73) Assignee: COVIDIEN LP, Mansfield, MA (US)

( * ) Notice: Subject to any disclaimer, the term of this patent is extended or adjusted under 35 U.S.C. 154(b) by 1054 days.

(21) Appl. No.: 13/421,627

(22) Filed: Mar. 15, 2012

(65) Prior Publication Data

US 2012/0220846 A1 Aug. 30, 2012

Related U.S. Application Data

(63) Continuation of application No. 12/409,688, filed on Mar. 24, 2009, now abandoned.

(60) Provisional application No. 61/072,095, filed on Mar. 27, 2008.

(51) Int. Cl.
*A61B 5/02* (2006.01)
*A61B 5/1455* (2006.01)
*A61B 5/00* (2006.01)

(52) U.S. Cl.
CPC ........... *A61B 5/14551* (2013.01); *A61B 5/4818* (2013.01)

(58) Field of Classification Search
CPC ............ A61B 5/14551; A61B 5/4818; A61B 5/0205; A61B 5/021
See application file for complete search history.

(56) References Cited

U.S. PATENT DOCUMENTS

| | | | |
|---|---|---|---|
| 6,342,039 B1 * | 1/2002 | Lynn et al. | 600/529 |
| 7,398,115 B2 | 7/2008 | Lynn | |

* cited by examiner

*Primary Examiner* — Michael Kahelin
*Assistant Examiner* — Tho Tran
(74) *Attorney, Agent, or Firm* — Fletcher Yoder PC

(57) ABSTRACT

Various embodiments may provide methods and systems capable of evaluating physiological parameter data. The methods and systems may include monitoring a patient to produce a signal comprising a sequence of numerical values for blood oxygen saturation over a time period. The signal may be analyzed to identify two or more desaturation patterns within the time period, and at least two numerical differences are calculated between the desaturation patterns. A saturation pattern detection index may be calculated using the numerical differences between the desaturation patterns. The saturation pattern detection index may be used to provide an indication of a physiological condition. Other embodiments may provide a medical device that may be used to evaluate physical parameter data according to the techniques described.

16 Claims, 10 Drawing Sheets

SYSTEM AND METHOD FOR DIAGNOSING SLEEP APNEA

RELATED APPLICATIONS

This application claims priority to U.S. patent application Ser. No. 12/409,688 filed Mar. 24, 2009, which in turn claims priority to U.S. Provisional Application No. 61/072,095 filed Mar. 27, 2008, which are both incorporated herein by reference in their entirety.

BACKGROUND

Embodiments of the present disclosure may relate to a system and method for evaluating physiological parameter data. Specifically, for example, an embodiment may include a medical device capable of calculating a saturation pattern detection index (SPDi) based on pulse oximetry data.

This section is intended to introduce the reader to various aspects of art that may be related to various aspects of the present disclosure, which are described and/or claimed below. This discussion is believed to be helpful in providing the reader with information to facilitate a better understanding of the disclosure. Accordingly, it should be understood that these statements are to be read in this light, and not as admissions of prior art.

Obstructive sleep apnea is a condition in which a patient's breathing is temporarily interrupted when sleeping. The condition is believed to be associated with increased fat deposits in the neck, which commonly occur as a patient ages. These increased fat deposits may lead to a narrowing of the airway. When muscle tone diminishes during sleep the narrowed airway can collapse during inhalation, effectively choking off air movement. The choking patient may attempt to inhale more deeply, which typically results in further collapsing the airway. With no air movement, the oxygen level in the patient's bloodstream typically falls, finally reaching a point where the patient is aroused out of sleep. Upon arousal, the muscle tone increases, the airway opens, and air flow to the lungs is precipitously restored. The patient hyperventilates, which quickly restores the blood oxygen levels to normal levels. The period of arousal is brief, so the patient is often unaware that the event took place. The patient returns to sleeping, and the cycle often repeats.

Over the years, this repeating cycle of low oxygen levels in the bloodstream can damage the heart and lead to other serious medical complications. Obstructive sleep apnea is believed to be one of the most common disorders in the United States and an important cause of heart attack and stroke. However, unlike other common medical disorders, such as diabetes, no simple diagnostic test has been developed to determine if a patient has sleep apnea. Tests do exist that can be used to diagnose sleep apnea, but the tests typically involve an overnight sleep study, which can be costly and inconvenient. The need for a simple, low-cost diagnostic test has led medical personnel to try less expensive techniques, such as pulse oximetry, to diagnose the presence of obstructive sleep apnea.

SUMMARY

Embodiments disclosed herein may include methods and systems capable of evaluating a physiological parameter. The method may include monitoring a patient to produce physiological parameter data comprising a sequence of numerical values for blood oxygen saturation over a time period. The physiological parameter data may be analyzed to identify two or more desaturation patterns within the time period. Differences between the two or more desaturation patterns may be determined. A saturation pattern detection index may be calculated based at least in part upon the differences between the desaturation patterns. The saturation pattern detection index may be used to provide an indication of a physiological condition.

Another embodiment may include a medical system. The medical system may include a sensor that is capable of producing physiological parameter data comprising a sequence indicative of blood oxygen level over a time period. The medical system may also include a microprocessor that is configured to process the physiological parameter data, and a memory that is configured for storing computer-readable instructions. The contents of the memory may include computer-readable instructions configured to direct the microprocessor to obtain the physiological parameter data from the sensor, analyze the physiological parameter data to identify two or more desaturation patterns within the time period, determine differences between the desaturation patterns, calculate a saturation pattern detection index based at least in part upon the differences, and provide an indication of a physiological condition based at least in part upon the saturation pattern detection index.

Another embodiment may include a computer-readable medium including computer readable code that, when executed, may obtain physiological parameter data from a measurement device monitoring a patient, wherein the physiological parameter data includes values for blood oxygen saturation taken over a time period. The computer-readable medium may also include computer readable code configured to analyze the physiological parameter data to identify two or more desaturation patterns within the time period, determine differences between the desaturation patterns, calculate a saturation pattern detection index based at least in part upon the differences, and provide an indication of a physiological condition based at least in part upon the saturation pattern detection index.

BRIEF DESCRIPTION OF THE DRAWINGS

Advantages of the techniques may become apparent upon reading the following detailed description and upon reference to the drawings in which.

DETAILED DESCRIPTION

Figure 1:
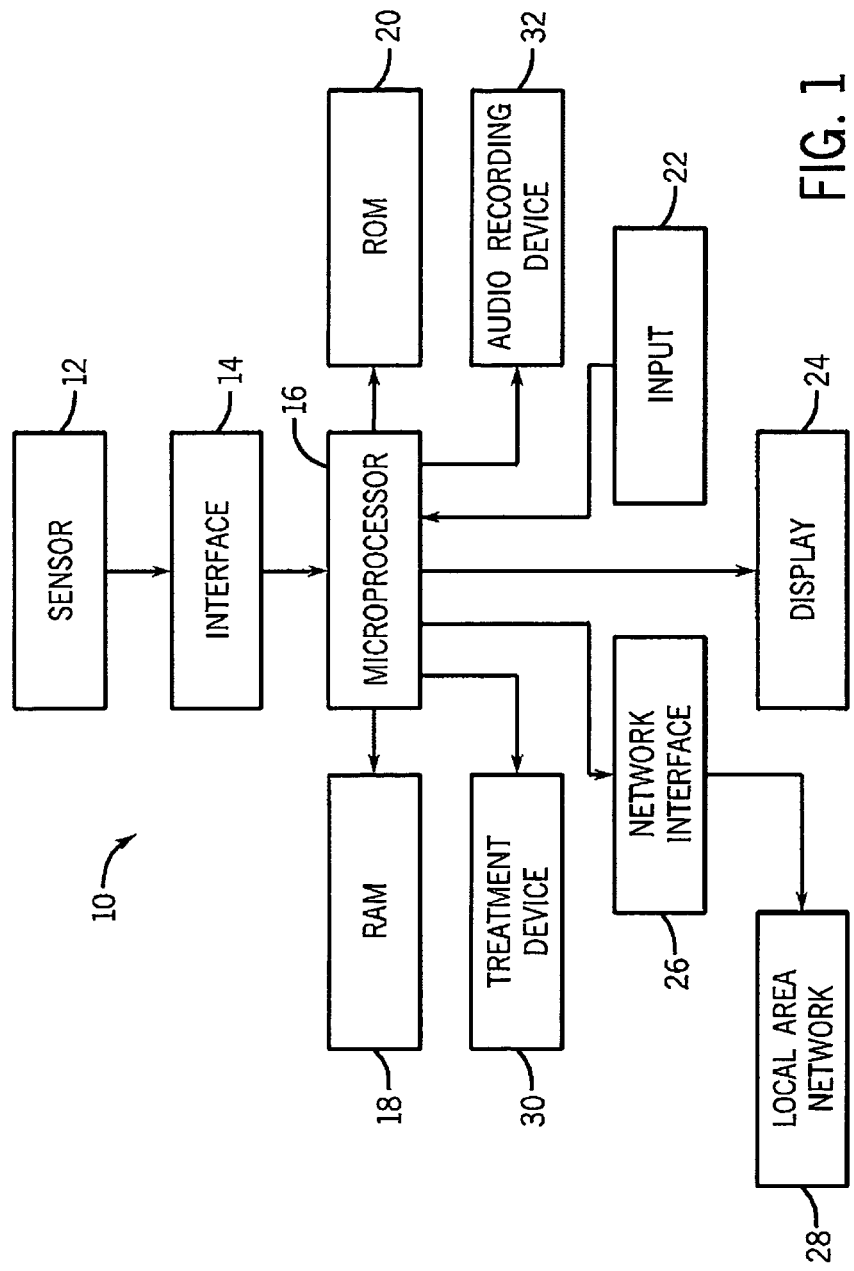
FIG. 1 is a block diagram of a system for the diagnosis and treatment of sleep apnea, in accordance with various embodiments.

One or more embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for one of ordinary skill having the benefit of this disclosure.

Medical devices may be used to obtain signals representing physiological parameters from patients. However, these signals, which are sequences of numerical values of a physiological parameter over time, may have too much information or noise to be effectively used in the diagnosis or treatment of certain medical conditions. Accordingly, the signals may be processed to generate a secondary series of numerical values over time, termed an index, which may provide a more useful representation of the status of the medical condition. Embodiments may include methods that may be useful for calculating an index representing saturation pattern detection from a signal representing the blood oxygen saturation (SpO$_2$) level in a patient.

The saturation pattern detection index (SPDi) may be directly related to the presence and/or severity of obstructive sleep apnea and, thus, may assist practitioners in the diagnosis and treatment of this condition. The SPDi may be defined as a scoring metric associated with the identification of a saturation trend pattern generated in accordance with present embodiments and may correlate to ventilatory instability in a population of sleep lab patients. In various embodiments, SpO$_2$ data collected with a pulse oximeter may be used to calculate the SPDi. The relative simplicity of this device could enhance the diagnosis of obstructive sleep apnea by allowing patients to take diagnostic equipment home for use overnight and return the equipment to a practitioner for analysis and diagnosis.

Various embodiments may provide techniques for generating an SPDi from an SpO$_2$ signal using the relative changes in the signal to identify patterns and calculate the index. As other indications of the severity of the physiological condition may be used to activate alarms, either alone or in conjunction with the value of the SPDi calculated below, the techniques of the present disclosure may be implemented using current medical devices, easing their implementation on current medical devices. Traditional oximetry alarms may be triggered by absolute SpO$_2$ threshold crossings. Therefore, an SPDi based on only relative changes in SpO$_2$ may be advantageous because it may provide additional information to the caregiver and may not conflict with or duplicate existing SpO$_2$ alarms.

FIG. 1 is a block diagram of a medical device 10, according to various embodiments. The medical device 10 may have a sensor 12 for the collection of a signal representing a physiological parameter. In an embodiment, the sensor 12 may be an optical sensor used with a pulse oximeter for the measurement of oxygen saturation (SpO$_2$) in the bloodstream. The SpO$_2$ signal from the sensor 12 may be conditioned by an interface 14 prior to being utilized by a microprocessor 16. The microprocessor 16 may be connected to random access memory (RAM) 18 and/or read-only memory (ROM) 20. The RAM 18 may be used to store the signals from the sensor 12 and the results of calculations that the microprocessor 16 performs. The ROM 20 may contain code to direct the microprocessor 16 in collecting and processing the signal. The microprocessor 16 may be connected to an input device 22 which may be used for local entry of control and calculation parameters for the medical device 10. A display unit 24 may be connected to the microprocessor 16 to display the results the microprocessor 16 has generated from the signal.

The microprocessor 16 may also be connected to a network interface 26 for the transfer of data from the microprocessor 16 to devices connected to a local area network 28. The transferred data may, for example, include signal data, indices including an SPDi, alarm signals, or any combination thereof. The transferred data may also consist of control signals from the devices on the local area network 28, for example, to instruct the medical device 10 to send signal data, or other information, to a device on the local area network 28.

In an embodiment, the medical device 10 may be used to calculate an SPDi with the data collected from the sensor 12, using the method discussed below. The SPDi may be output to the display unit 24 or sent to a network device on the local area network 28. The processing may take place in real time, or may be run after the data collection is completed for later determination of an index representing a physiological parameter.

In another embodiment, a network device located on the local area network 28 may be used to calculate an SPDi with the data collected from the sensor 12, using the method discussed below. In this embodiment, the network device may request that the signal be sent from the medical device 10 through the network interface 26. As for the embodiment discussed above, the network device may be used to either determine the SPDi in real time or to process a previously collected signal to generate the SPDi.

In various embodiments, the value of the SPDi may be used to trigger one or more alarms, alerting practitioners to clinically important conditions. These alarms may appear on devices on the local area network 28, such as on a patient monitoring screen in an ICU. Alternatively, the alarms may appear on the display unit 24 of the medical device 10. Further, it may be advantageous to activate alarms in both locations using the results from either a local calculation on the medical device 10 or from a remote calculation on a network device connected to the local area network 28.

Furthermore, the microprocessor 16 may be connected to a treatment device 30. For example, the treatment device may be a positive pressure mask used to supply air at an increased pressure to maintain an open airway. In an embodiment, the treatment device may be controlled by the microprocessor 16, for example, activating the treatment device 30 to open an airway based on the value of the SPDi. This action may be useful in helping to confirm a diagnosis of obstructive sleep apnea, as restoration of the airway may restore blood oxygen levels to normal and, thus, lower the SPDi. The treatment device 30 may be activated instead of, or in addition to, any alarms discussed above.

A diagnosis of sleep apnea may also be aided by the sound the patient is making during putative sleep apnea events. For example, cessation of breathing followed by a sudden gasping intake of breath may provide or confirm a diagnosis. However, such events may be irregularly spaced or may be separated by large time intervals, making any continuous audio recording of the patient tedious and/or expensive to analyze. In an embodiment, an audio recording device 32 may be connected to the microprocessor 16 for recording sounds made by the patient. In an embodiment, the microprocessor 16 may activate the audio recording device 32 based on the SPDi and record patient sounds when a sleep apnea event is likely to be occurring. When combined with the SPDi, the sound recordings may provide a positive diagnosis of obstructive sleep apnea.

Figure 2:
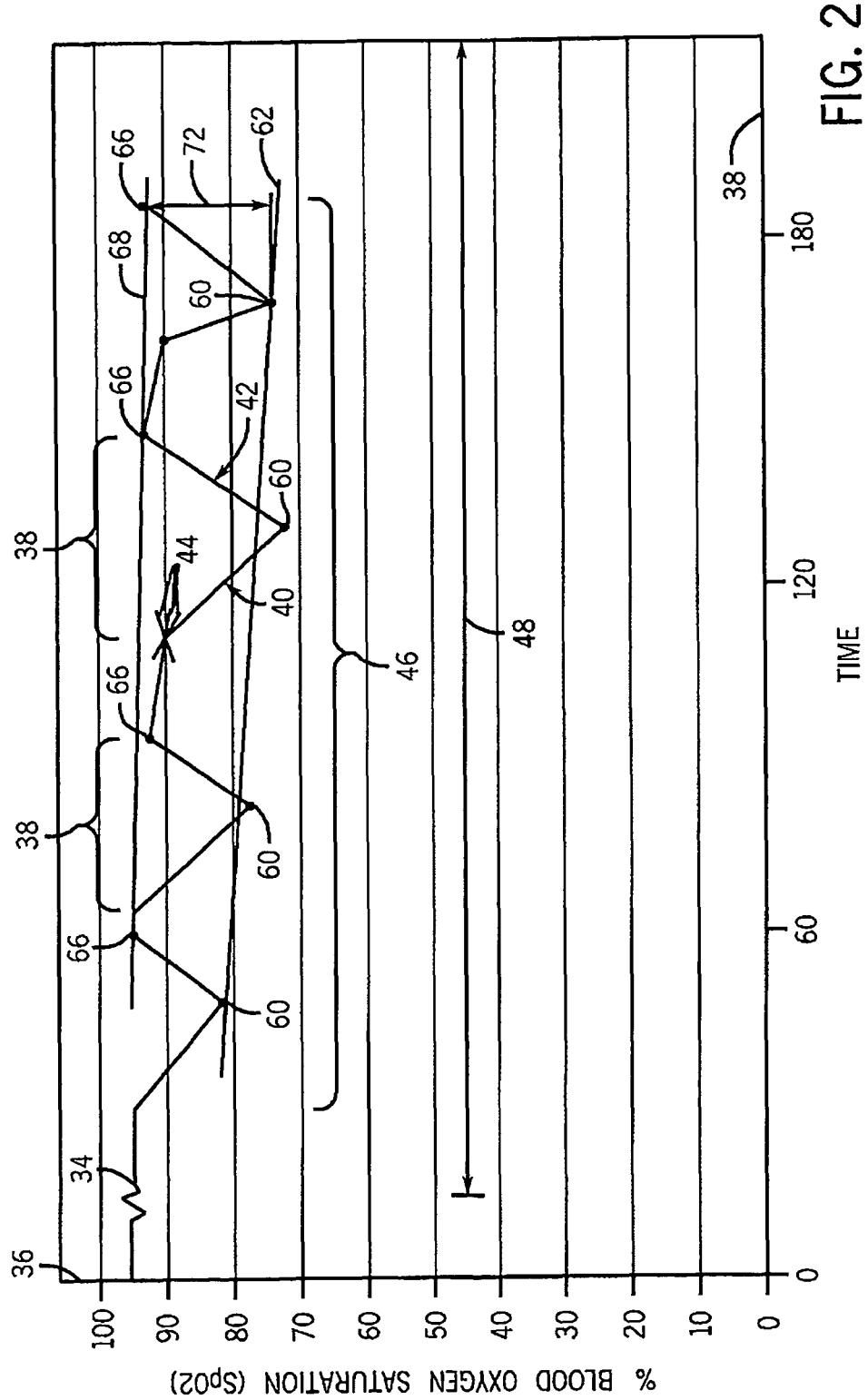
FIG. 2 is a chart of $SpO_2$ data over time illustrating techniques that may be used for calculating differences between oxygen desaturation patterns during obstructive sleep apnea, in accordance with various embodiments.

FIG. 2 is a chart of a sequence of values representing the blood oxygen saturation ($SpO_2$) of a patient over time, i.e., a $SpO_2$ signal 34. In this chart, the left vertical axis 36 represents the $SpO_2$ level. The horizontal axis 38 represents the time in seconds. In an embodiment, a pattern analysis method may be used to identify obstructive sleep apnea and calculate an SPDi from the $SpO_2$ signal 34. The method indicates that during each sleep apnea event, called a desaturation pattern 38, the blood oxygen level falls slowly, as indicated by reference numeral 40, as oxygen stores in the body are used up and then sharply recovers, as indicated by reference numeral 42, as the patient is aroused and hyperventilates.

In various embodiments, the determination of the presence of a desaturation pattern 38 may be performed by any number of different techniques. In an embodiment, a desaturation pattern 38 may be identified by calculating a derivative of the $SpO_2$ signal 34 over an 8 second rolling window. A nadir point, which may be defined as a minimum $SpO_2$ value in a reciprocation, may then be detected when the derivative changes from a negative to positive value. Similarly, a peak may be detected when the derivative changes from a positive to negative value. Peaks may include a rise peak (e.g., a maximum $SpO_2$ value in a reciprocation that occurs after the nadir) and/or a fall peak (e.g., a maximum $SpO_2$ value in a reciprocation that occurs before the nadir). The derivative could be calculated over a window of any length. For example, reducing the length of the window to 4 would allow the method to detect shorter desaturation events, but may make the method more susceptible to noise. Increasing the length to 16 seconds may make the detection method less susceptible to noise but less sensitive to shorter duration desaturation events. The derivative window could be fixed, as described above, or could adapt based on other metrics computed within the oximetry system.

Figure 3:
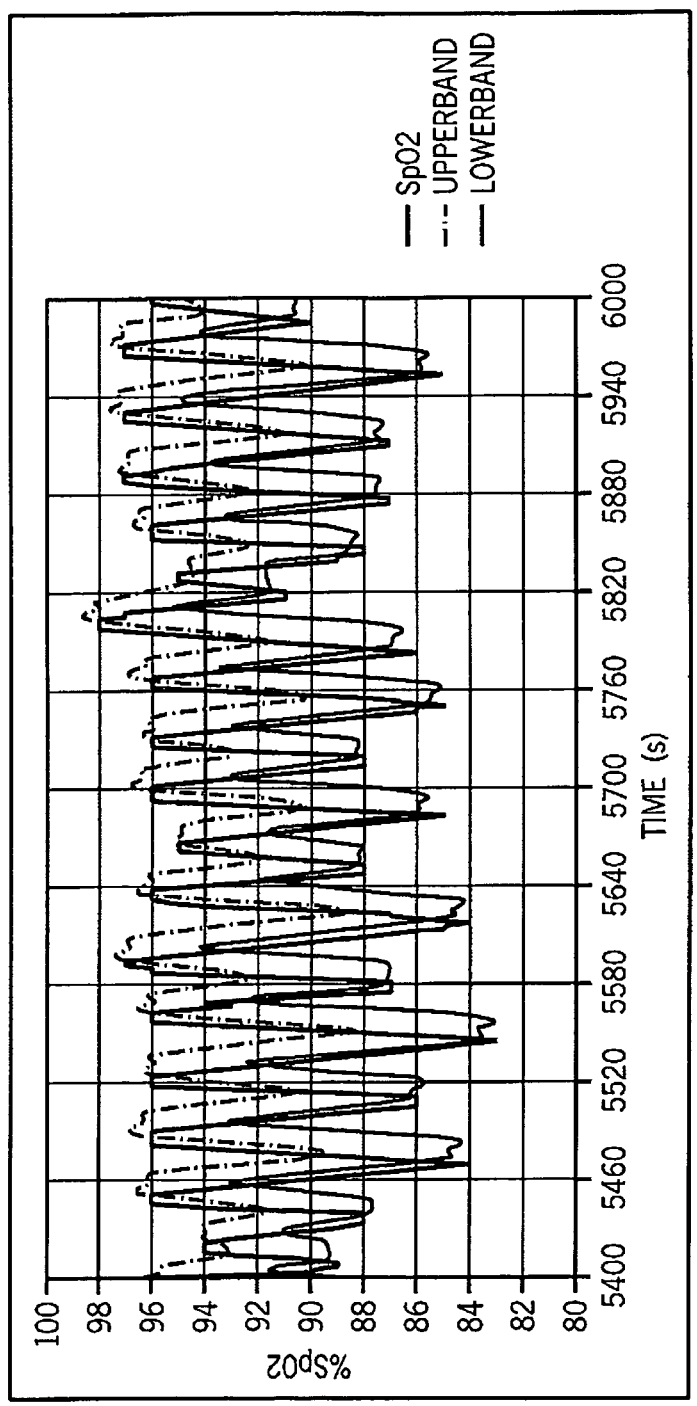
FIG. 3 is a chart of $SpO_2$ data including an upper band and lower band relative to the $SpO_2$ trend to facilitate detection of peaks and nadirs in accordance with various embodiments.

In one embodiment, the medical device 10 may include hardware and/or software features that are configured to perform a statistical method to find potential reciprocation peaks and nadirs in a trend of $SpO_2$ data. Once per second, a rolling mean and standard deviation (e.g., a 12 second rolling mean and standard deviation) of the $SpO_2$ trend may be calculated. Further, based on these mean and standard deviation values, an upper band and lower band with respect to an $SpO_2$ trend, as illustrated by FIG. 3, may be calculated as follows:

Upper Band=mean+standard deviation;

Lower Band=mean−standard deviation.

Once the upper band and lower band have been determined, potential reciprocation peaks and nadirs may be extracted from the $SpO_2$ trend using the upper band and the lower band. Indeed, a potential peak may be identified as the highest $SpO_2$ point in a trend segment which is entirely above the upper band. Similarly, a potential nadir may be identified as the lowest $SpO_2$ point in a trend segment that is entirely below the lower band. In other words, identified peaks may be at least one standard deviation above the rolling mean, and identified nadirs may be at least one standard deviation below the mean. If there is more than one minimum value below the lower band, the last (or most recent) trend point may be identified as a nadir. If more than one maximum value is above the upper band, the point identified as a peak may depend on where it is in relation to the nadir. For example, regarding potential peaks that occur prior to a nadir (e.g., fall peaks), the most recent maximum trend point may be used. In contrast, for peaks that occur subsequent to a nadir (e.g., rise peaks), the first maximum point may be used. In the example trend data represented in FIG. 3, a peak and nadir is detected approximately every 30-60 seconds.

In one embodiment, a window size for calculating the mean and standard deviation may be set based on historical values (e.g., average duration of a set number of previous reciprocations). For example, in one embodiment, a window size for calculating the mean and standard deviation may be set to the average duration of all qualified reciprocations in the last 6 minutes divided by 2. In another embodiment, a dynamic window method may be utilized wherein the window size may be initially set to 12 seconds and then increased as the length of qualified reciprocations increases. This may be done in anticipation of larger reciprocations because reciprocations that occur next to each other tend to be of similar shape and size. If the window remained at 12 seconds, it could potentially be too short for larger reciprocations and may prematurely detect peaks and nadirs. The following equation or calculation is representative of a window size determination, wherein the output of the filter is inclusively limited to 12-36 seconds, and the equation is executed each time a new reciprocation is qualified:

If no qualified reciprocations in the last 6 minutes:

Window Size=12(initial value)

else:

RecipDur=½*current qualified recip duration+½*previous RecipDur

Window Size=bound(RecipDur,12,36).

With regard to $SpO_2$ signals that are essentially flat, the dynamic window method may fail to find the three points (i.e., a fall peak, a rise peak, and a nadir) utilized to identify a potential reciprocation. Therefore, present embodiments may limit the amount of time that the dynamic window method can search for a potential reciprocation. For example, if no reciprocations are found in 240 seconds plus the current dynamic window size, the medical device 10 may be configured to timeout the algorithm and begin to look for potential reciprocations at the current $SpO_2$ trend point and later. The net effect of this may be that potential reciprocations less than 240 seconds long are detected.

Once the peaks and nadirs of each desaturation pattern 38 have been detected, any number of selection features could be calculated to qualify the desaturation pattern 38. For example, in an embodiment, the slope of the line 44 connecting the peak and nadir could be used. When the slope 44 of the $SpO_2$ signal 34 is less than a previously selected value, e.g. −1.5, the desaturation pattern 38 would be detected. The method would not detect a desaturation pattern 38 when the slope 44 is above or equal to −1.5. Embodiments may include any number of different values, which may be used for these determinations, for example, in an embodiments the value of the slope selected to indicate the start of a desaturation pattern 38 may be −0.5, −1.0, −1.5, −2, or any value in between. The slope is just one example of a feature that may be selected. Any number of other parameters may be calculated from the detected peak and nadir and used to detect a desaturation pattern 38. Further, any combination of parameters may be used to detect the desaturation pattern 38.

In one embodiment, once the potential peaks and nadirs are identified, a determination may be made as to whether potential reciprocations are qualified using stages of qualification criteria. Indeed, potential reciprocations may be passed through one or more qualification stages to determine if a related event is caused by ventilatory instability. A first qualification stage may include checking reciprocation metrics against a set of limits (e.g., predetermined hard limits). A second qualification stage may include a linear qualification function. In accordance with present embodiments, a reciprocation may be required to pass through both stages in order to be qualified.

As an example, in a first qualification stage, which may include a limit-based qualification, four metrics may be calculated for each potential reciprocation and compared to a set of limits. Any reciprocation with a metric that falls outside of these limits may be disqualified. The limits may be based on empirical data. For example, in some embodiments, the limits may be selected by calculating the metrics for potential reciprocations from sleep lab data where ventilatory instability is known to be present, and then comparing the results to metrics from motion and breathe-down studies. The limits may then be refined to filter out true positives.

The metrics referred to above may include fall slope, magnitude, slope ratio, and path length ratio. With regard to fall slope, it may be desirable to limit the maximum fall slope to filter out high frequency artifact in the $SpO_2$ trend, and limit the minimum fall slope to ensure that slow $SpO_2$ changes are not qualified as reciprocations. Regarding magnitude, limits may be placed on the minimum magnitude because of difficulties associated with deciphering the difference between ventilatory instability reciprocations and artifact reciprocations as the reciprocation size decreases, and on the maximum magnitude to avoid false positives associated with sever artifact (e.g., brief changes of more than 35% $SpO_2$ that are unrelated to actual ventilatory instability). The slope ratio may be limited to indirectly limit the rise slope for the same reasons as the fall slope is limited and because ventilatory instability patterns essentially always have a desaturation rate that is slower than the resaturation (or recovery) rate. The path length ratio may be defined as Path Length/((Fall Peak−Nadir)+(Rise Peak−Nadir)), where Path Length=Σ|Current $SpO_2$ Value−Previous $SpO_2$ value| for all $SpO_2$ values in a reciprocation, and the maximum path length ratio may be limited to limit the maximum standard deviation of the reciprocation, which limits high frequency artifact. The following table (Table I) lists the above-identified metrics along with their associated equations and the limits used in accordance with one embodiment:

TABLE I

| Metric | Equation | Minimum | Maximum |
|---|---|---|---|
| Fall Slope | (Nadir − Fall Peak)/Time between Fall Peak and Nadir | −1.6 (Fast Response Mode) −1 (Normal Response Mode) | −0.08 (Fast Response Mode) −0.05 (Normal Response Mode) |
| Magnitude | Max(Rise Peak, Fall Peak) − Nadir | 3 | 35 |
| Slope Ratio | |Fall Slope/Rise Slope| | 0.05 | 1.75 |
| Path Length Ratio | Path Length = Σ|Current $SpO_2$ Value − Previous $SpO_2$ Value| for all $SpO_2$ values in a Reciprocation. Path Length Ratio = Path Length/((Fall Peak − Nadir) + (Rise Peak − Nadir)) | N/A | 2 |

As indicated in Table I above, an oximetry algorithm in accordance with present embodiments may operate in two response modes: Normal Response Mode or Fast Response Mode. The selected setting may change the $SpO_2$ filtering performed by the oximetry algorithm, which in turn can cause changes in $SpO_2$ patterns. Therefore a saturation pattern detection feature may also accept a response mode so that it can account for the different $SpO_2$ filtering. Table I indicates values associated with both types of response mode with regard to the Fall Slope values.

A second qualification stage may utilize an object reciprocation qualification feature. Specifically, the second qualification stage may utilize a linear qualification function based on ease of implementation, efficiency, and ease of optimization. The equation may be determined by performing a least squares analysis. For example, such an analysis may be performed with MATLAB®. The inputs to the equation may include the set of metrics described below. The output may be optimized to a maximum value for patterns where ventilatory instability is known to be present. The equation may be optimized to output smaller values (e.g., 0) for other data sets where potential false positive reciprocations are abundant.

To simplify optimization, the equation may be factored into manageable sub-equations. For example, the equation may be factored into sub-equation 1, sub-equation D, and sub-equation 2, as will be discussed below. The output of each sub-equation may then be substituted into the qualification function to generate an output. The outputs from each of the sub-equations may not be utilized to determine whether a reciprocation is qualified in accordance with present embodiments. Rather, an output from a full qualification function may be utilized to qualify a reciprocation. It should be noted that the equations set forth in the following paragraphs describe one set of constants. However, separate sets of constants may be used based on the selected response mode. For example, a first set of constants may be used for the Normal Response Mode and a second set of constants may be used for the Fast Response Mode.

Preprocessing may be utilized in accordance with present embodiments to prevent overflow for each part of the qualification function. The tables (Tables II-VII) discussed below, which relate to specific components of the qualification function may demonstrate this overflow prevention. Each row in a table contains the maximum value of term which is equal to the maximum value of the input variable multiplied by the constant, wherein the term "maximum" may refer to the largest possible absolute value of a given input. Each row in a table contains the maximum intermediate sum of the current term and all previous terms. For example, a second row may contain the maximum output for the second term calculated, as well as the maximum sum of terms 1 and 2. It should be noted that the order of the row may match the order that the terms are calculated by the medical device 10. Further, it should be noted that in the tables for each sub-equation below, equations may be calculated using temporary signed 32-bit integers, and, thus, for each row in a table where the current term or intermediate term sum exceeds 2147483647 or is less than −2147483647 then an overflow/underflow condition may occur.

A first sub-equation, sub-equation 1, may use metrics from a single reciprocation. For example, sub-equation 1 may be represented as follows:

Eq1Score=SlopeRatio*SrCf+PeakDiff*PdCf+
FallSlope*FsCf+PathRatio*PrCf+Eq1Offset, where SrCf, PdCf, FsCf, PrCf, and Eq1Offset may be selected using least squares analysis (e.g., using MATLAB®). PeakDiff may be defined as equal to |Recip Fall Peak−Recip Rise Peak|. It should be noted that PeakDiff is typically not considered in isolation but in combination with other metrics to facilitate separation. For example, a true positive reciprocation which meets other criteria but has a high peak difference could be an incomplete recovery. That is, a patient's $SpO_2$ may drop from a baseline to a certain nadir value, but then fail to subsequently recover to the baseline. However, when used in combination with other metrics in the equation, PeakDiff may facilitate separation of two classifications, as large peak differences are more abundant in false positive data sets.

With regard to sub-equation 1, the tables (Tables II and III) set forth below demonstrate that the inputs may be preprocessed to prevent overflow. Further, the tables set forth below include exemplary limits that may be utilized in sub-equation 1 in accordance with present embodiments. It should be noted that Table II includes Fast Response Mode constants and Table III includes Normal Response Mode constants.

A second sub-equation, sub-equation D, may correspond to a difference between two consecutive reciprocations which have passed the hard limit qualifications checks, wherein consecutive reciprocations include two reciprocations that are separated by less than a defined time span. For example, consecutive reciprocations may be defined as two reciprocations that are less than 120 seconds apart. The concept behind sub-equation D may be that ventilatory instability tends to be a relatively consistent event, with little change from one reciprocation to the next. Artifact generally has a different signature and tends to be more random with greater variation among reciprocations. For example, the following equation may represent sub-equation D:

EqD=SlopeRatioDiff*SrDCf+DurationDiff*DDCf+
NadirDiff*NdCf+
PathLengthRatioDiff*PrDCf_EqDOffset, where, SrDCf, DDCf, NdCf, PrDCf, and EqDOffset may be selected using least squares analysis (e.g., using MATLAB®). With regard to other variables in sub-equation D, SlopeRatioDiff may be defined as |Current Recip Slope Ratio−Slope Ratio of last qualified Recip|; DurationDiff may be defined as |Current Recip Duration−Duration of last qualified Recip|; NadirDiff may be defined as |Current Recip Nadir−Nadir value of last qualified Recip|; and PathLengthRatioDiff may be defined as |Current Recip Path Length Ratio−Path Length Ratio of last qualified Recip|.

With regard to sub-equation D, the tables (Tables IV and V) set forth below demonstrate that the inputs may be preprocessed to prevent overflow. Further, the tables set forth below include exemplary limits that may be utilized in sub-equation D in accordance with present embodiments. It should be noted that Table IV includes Fast Response Mode constants and Table V includes Normal Response Mode constants

TABLE II

| Term | Variable Type | Maximum Variable Value (a) | Variable Preprocessing | Constant Value (b) (Fast Mode) | Maximum Term Value (a * b) | Maximum Intermediate Sum (sum of all previous rows) | Overflow |
|---|---|---|---|---|---|---|---|
| PeakDiff * PdCf | U8 | 100 | None. This value may not exceed 100 since the maximum $SpO_2$ value accepted is 100 | −29282 | −2928200 | −2928200 | NO |
| SlopeRatio * SrCf | U8 | 255 | None | −1534 | −391170 | −3319370 | NO |
| FallSlope * FsCf | S16 | −32768 | None | −19 | 622592 | −2696778 | NO |
| PathRatio * PrCf | U16 | 65535 | None | −7982 | −523100370 | −525797148 | NO |
| Eq1Offset | N/A | N/A | N/A | 809250 | 809250 | −524987898 | NO |

TABLE III

| Term | Variable Type | Maximum Variable Value (a) | Variable Preprocessing | Constant Value (b) (Normal Mode) | Maximum Term Value (a * b) | Maximum Intermediate Sum (sum of all previous rows) | Overflow |
|---|---|---|---|---|---|---|---|
| PeakDiff *PdCf | U8 | 100 | None. This value may not exceed 100 since the maximum $SpO_2$ value accepted is 100 | −33311 | −3331100 | −3331100 | NO |
| SlopeRatio * SrCf | U8 | 255 | None | −2151 | −548505 | −3879605 | NO |
| FallSlope * FsCf | S16 | −32768 | None | −706 | 23134208 | 19254603 | NO |
| PathRatio * PrCf | U16 | 65535 | None | −6178 | −404875230 | −385620627 | NO |
| Eq1Offset | N/A | N/A | N/A | 576330 | 576330 | −385044297 | NO |

TABLE IV

| Term | Variable Type | Maximum Variable Value (a) | Variable Preprocessing | Constant Value (b) (Fast Mode) | Maximum Term Value (a * b) | Maximum Intermediate Sum (sum of all previous rows) | Overflow |
|---|---|---|---|---|---|---|---|
| EqDOffset | N/A | N/A | N/A | 885030 | 885030 | 885030 | NO |
| SlopeRatioDiff * SrDCf | U8 | 255 | None | −2809 | −716295 | 168735 | NO |
| DurationDiff * DDCf | U16 | 240 | The Recip detection module may only detect recips less than or equal to 240 seconds long | −2960 | −710400 | −541665 | NO |
| NadirDiff * NdCf | U8 | 100 | This value may not exceed 100 since the maximum SpO$_2$ value accepted is 100 | −13237 | −1323700 | −1865365 | NO |
| PathLengthRatioDiff * PrDCf | U16 | 65535 | None | −7809 | −511762815 | −513628180 | NO |

TABLE V

| Term | Variable Type | Maximum Variable Value (a) | Variable Preprocessing | Constant Value (b) (Normal Mode) | Maximum Term Value (a * b) | Maximum Intermediate Sum (sum of all previous rows) | Overflow |
|---|---|---|---|---|---|---|---|
| EqDOffset | N/A | N/A | N/A | 847650 | 847650 | 847650 | NO |
| SlopeRatioDiff * SrDCf | U8 | 255 | None | −2629 | −670395 | 177255 | NO |
| DurationDiff * DDCf | U16 | 240 | The Recip detection module may only detect recips less than or equal to 240 seconds long | −4282 | −1027680 | −850425 | NO |
| NadirDiff * NdCf | U8 | 100 | This value may not exceed 100 since the maximum SpO$_2$ value accepted is 100 | −11705 | −1170500 | −2020925 | NO |
| PathLengthRatioDiff * PrDCf | U16 | 65535 | None | −7844 | −514056540 | −516077465 | NO |

A third sub-equation, sub-equation 2, may combine the output of sub-equation D with the output of sub-equation 1 for a reciprocation (e.g., a current reciprocation) and a previous reciprocation. For example, the following equation may represent sub-equation 2:

Eq2Score=EqDScore*DCf+
 Eq1ScoreCurrent*CurrEq1Cf+
 Eq1ScorePrev*PrevEq1Cf, where DCf, N1Cf, PrevEq1Cf, and Eq2Offset may be selected using least squares analysis (e.g., using MAT-LAB®). With regard to other variables in sub-equation 2, EqDScore may be described as the output of sub-equation D; Eq1ScoreCurrent may be described as the output of sub-equation 1 for a current reciprocation; and Eq1ScorePrev may be described as the output of sub-equation 1 for the reciprocation previous to the current reciprocation.

With regard to sub-equation 2, the tables (Tables VI and VII) set forth below demonstrate that the inputs may be preprocessed to prevent overflow. Further, the tables set forth below include exemplary limits that may be utilized in sub-equation 2 in accordance with present embodiments. It should be noted that Table VI includes Fast Response Mode constants and Table VII includes Normal Response Mode constants.

TABLE VI

| Term | Variable Type | Maximum Variable Value (a) | Variable Preprocessing | Constant Value (b) (Fast Mode) | Maximum Term Value (a * b) | Maximum Intermediate Sum (sum of all previous rows) | Overflow |
|---|---|---|---|---|---|---|---|
| Eq2Offset | N/A | N/A | N/A | −203800 | −203800 | −203800 | NO |
| EqDScore * DCf | S32 | −501590 | The largest output for sub-equation D may be −513628180 (see Table IV). The input value may be scaled by dividing the value by 1024. Therefore the largest input value may be −501590 | 529 | −265341110 | −265544910 | NO |
| Eq1ScorePrev * PrevEq1Cf | S32 | −512683 | The largest output for sub-equation 1 may be −524987898 (see Table II). The input value may be scaled by dividing the value by 1024. Therefore the largest input value may be −512683 | 333 | −170723439 | −436268349 | NO |
| Eq1ScoreCurrent * CurrEq1Cf | S32 | −512683 | Same as previous row | 617 | −316325411 | −752593760 | NO |

TABLE VII

| Term | Variable Type | Maximum Variable Value (a) | Variable Preprocessing | Constant Value (b) (Normal Mode) | Maximum Term Value (a * b) | Maximum Intermediate Sum (sum of all previous rows) | Overflow |
|---|---|---|---|---|---|---|---|
| Eq2Offset | N/A | N/A | N/A | −194550 | −194550 | −194550 | NO |
| EqDScore * DCf | S32 | −503981 | The largest output for sub-equation D may be −516077465 (see Table V). The input value may be scaled by dividing the value by 1024. Therefore the largest input value may be −503981 | 532 | −268117892 | −268312442 | NO |
| Eq1ScorePrev * PrevEq1Cf | S32 | −376000 | The largest output for sub-equation 1 may be −385024297 (see Table III). The input value may be scaled by dividing the value by 1024. Therefore the largest input value may be −376000 | 496 | −186496000 | −454808442 | NO |
| Eq1ScoreCurrent * CurrEq1Cf | S32 | −376000 | Same as previous row | 406 | −152656000 | −607464442 | NO |

A qualification function may utilize the output of each of the equations discussed above (i.e., sub-equation 1, sub-equation D, and sub-equation 2) to facilitate qualification and/or rejection of a potential reciprocation. For example, the output of the qualification function may be filtered with an infinite impulse response filter, and the filtered output of the qualification function may be used to qualify or reject a reciprocation. An equation for an unfiltered qualification function output in accordance with present embodiments is set forth below:

QFUnfiltered=Eq1Score*SingleRecipWt*Eq2Cf+
N2Score*MultipleRecipWt*Eq2Cf+
NConsecRecip*ConsecCf+RecipMax*MaxCf+
Artifact %*ArtCf+QFOffset, where Eq2Cf, ConsecCf, MaxCf, ArtCf, and QFOffset may be selected using least squares analysis (e.g., using MATLAB®), and, as indicated above, Eq1Score may be defined as the output of sub-equation 1.

Other metrics in the unfiltered qualification function include SingleRecipWt, MultipleRecipWt, NConsecRecip, RecipMax, and Artifact %. With regard to SingleRecipWt and MultipleRecipWt, when there are two or more consecutive qualified reciprocations (e.g., qualified reciprocations that are less than 120 seconds apart) present, SingleRecipWt may equal 0 and MultipleRecipWt may equal 1. However, when only a single reciprocation is present, SingleRecipWt may equal 1 and MultipleRecipWt may equal 0.

NConseRecip, which may be defined as equal to max(NConsecRecip',QFConsecMax), may include a count of the number of consecutive reciprocations (e.g., reciprocations that are less than or equal to 120 seconds apart) that have passed the hard limit checks. The value for NConsecRecip may be reset to 0 whenever a gap between any two partially qualified reciprocations exceeds 120 seconds. This may be based on the fact that ventilatory instability is a relatively long lasting event as compared to artifact. Therefore, as more reciprocations pass the hard limit checks, the qualification function may begin qualifying reciprocations that were previously considered marginal. However, to guard against a situation where something is causing a longer term artifact event (e.g., interference from nearby equipment), the value may be clipped to a maximum value to limit the metrics influence on the qualification function output.

RecipMax, which may be defined as equal to max(Fall Peak, Rise Peak), may facilitate making decisions about marginal reciprocations. Indeed, marginal reciprocations with higher maximum $SpO_2$ values may be more likely to get qualified than marginal reciprocations with lower $SpO_2$ values. It should be noted that this metric works in tandem with the NConsecRecip metric, and multiple marginal reciprocations with lower maximum $SpO_2$ values may eventually, over a long period of time, get qualified due to the NConsecRecip metric.

The metric Artifact % may be defined as an artifact percentage that is equal to 100*Total Artifact Count/Recip Duration, where Total Artifact Count is the number of times and artifact flag was set during the reciprocation. Present embodiments may include many metrics and equations that are used to set the artifact flag. Because of this it is a generally reliable indication of the amount of artifact present in the oximetry system as a whole. Marginal reciprocations with a high Artifact % are less likely to be qualified than marginal reciprocations with a low (or 0) artifact percentage.

A last component of the qualification function may include an infinite impulse response (IIR) filter that includes coefficients that may be tuned manually using a tool (e.g., a spreadsheet) that models algorithm performance. The filtered qualification function may be represented by the following equation, which includes different constants for different modes (e.g., Fast Response Mode and Normal Response Mode):

QFFiltered=SingleRecipWt*QFUnfiltered+((1−a)
*QFUnfiltered+a*PrevQFFiltered)*MultipleRecipWt, where QFUnfiltered may be defined as the current unfiltered qualification function output; PrevQFFiltered may be defined as the previous filtered qualification function output; and where the constat "a" may be set to 0.34 for Fast Response Mode and 0.5 for Normal Response Mode.

The filtered output of the qualification function may be compared to a threshold to determine if the current reciprocation is the result of RAF (Reduction In Airflow) or artifact. The optimum threshold may theoretically be 0.5. However, an implemented threshold may be set slightly lower to bias the output of the qualification function towards qualifying more reciprocations, which may result in additional qualification of false positives. The threshold may be lowered because, as discussed below, a cluster determination portion of the algorithm performed by the medical device 10 may require a certain number (e.g., 5) of fully qualified reciprocations before an index may be calculated, and a certain number (e.g., at least 2) of consecutive qualified reciprocations (with no intervening disqualified reciprocations) within the set of fully qualified reciprocations. Since multiple reciprocations may be required, the clustering detection method may be biased toward filtering out false positives. Accordingly, the reciprocation qualification function threshold may be lowered to balance the two processes.

The recurring sleep apnea events may often occur in groups of at least two successive desaturation patterns 38, called a cluster 46. The severity of the apnea may be determined from, for example, the number of desaturation patterns 38 in each cluster 46, the time between each desaturation pattern 38, the slope of the drop 40 in the blood oxygen level during each desaturation pattern 38, and/or the slope of the recovery 42 of the blood oxygen level as the desaturation patterns ends, among others. The measurement may be dependent on the time period 48 selected for the measurement. In an embodiment, this time period 48 may be 180 seconds. Other time periods 48 may be used. In various embodiments, the time period 48 may be 60 seconds, 120 seconds, 180 seconds, 240 seconds, 300 seconds, or any number in between. In other embodiments, much longer time periods 48 may be used, for example, 600 seconds, 1200 seconds or even a longer time periods 48 may be appropriate. The time period 48 may determine the amount of history used to calculate the SPDi and, therefore, may affect the response time of the SPDi. Longer durations may result in a less responsive index. Shorter durations may be more responsive.

Figure 4:
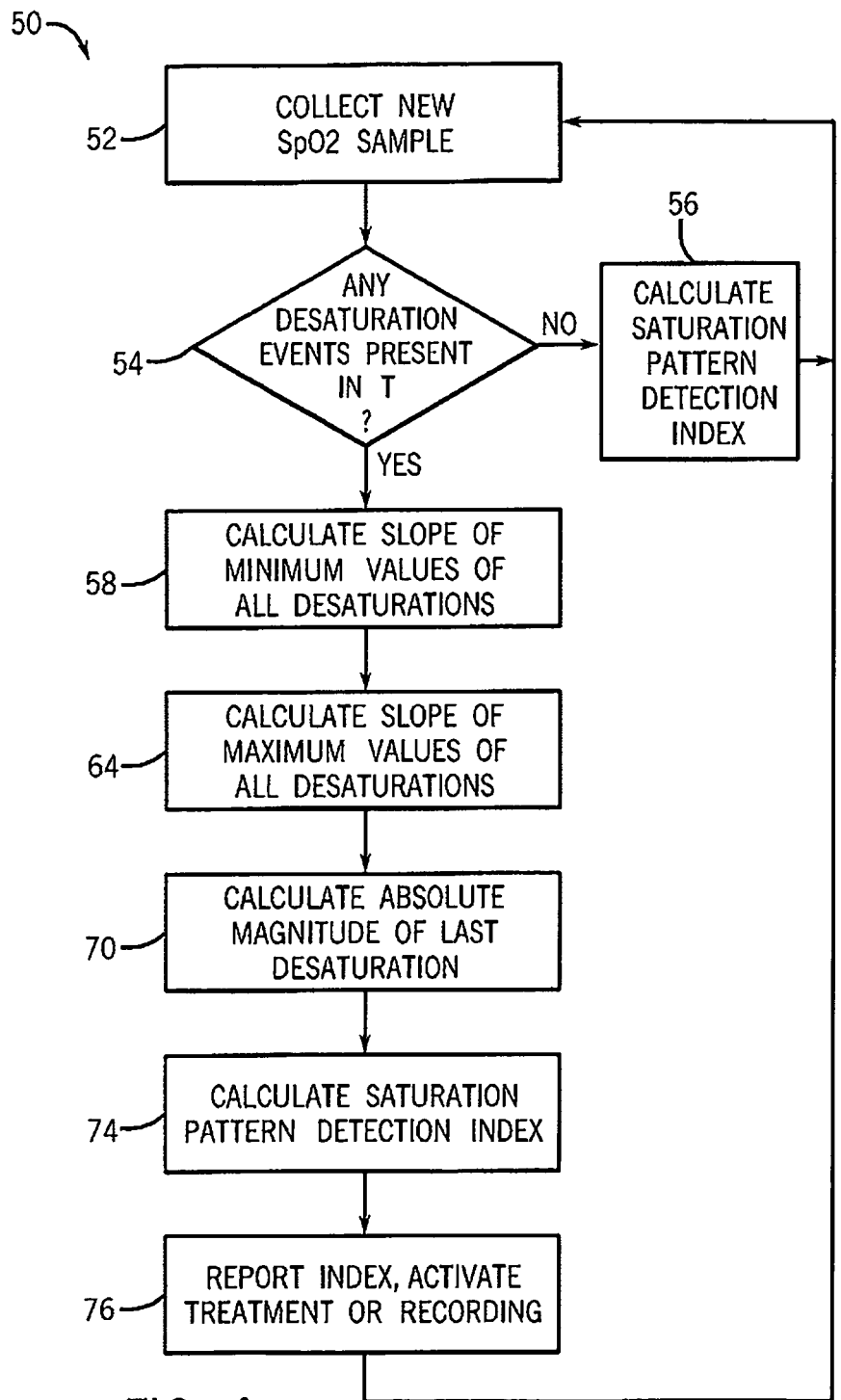
FIG. 4 is a process flow diagram showing an embodiment capable of generating an index representative of saturation pattern detection, in accordance with various embodiments.

FIG. 4 is a process flow diagram showing an embodiment of a method 50 for use in the calculation of an SPDi. Further details for calculating the SPDi may be found in U.S. Provisional Patent Application No. 61/110,299 filed Oct. 31, 2008, which is herein incorporated by reference in its entirety. The method 50 may include the collection of a new sample for the $SpO_2$ level as shown in block 52. Referring also to FIG. 2, over a time period 48 these samples provide the signal 34 representing the $SpO_2$ level. After the collection of each new $SpO_2$ sample, the signal 34 is analyzed to determine if any desaturation patterns 38 are present within the selected time period 48, as shown in block 54. This determination may be performed by the method discussed with respect to FIG. 2, above. If no desaturation patterns 38 are present, the SPDi is set to zero, as shown in block 56, and the method 50 returns to block 52 to collect another $SpO_2$ sample. If a desaturation pattern 38 is present, the method proceeds to block 58.

According to an embodiment, if a desaturation pattern 38 is present, a minimum value (e.g., value 60) of the $SpO_2$ level for each desaturation pattern 38 within the selected time period 48 may be determined, as shown in block 58. Referring again to FIG. 2, in an embodiment, the minimum values 60 may correspond to the lowest points of each desaturation pattern 38. However, other values may be selected. In an embodiment, a value may be selected that is several points in the signal before the actual minimum value 60. Such a selection may be useful in case the signal 34 overshoots the actual minimum value 60 due to measurement error.

After the minimum values 60 are identified, in block 58 of FIG. 4 a slope for the minimum values 60 may be calculated, as indicated by reference numeral 62 in FIG. 2. This slope may be termed the nadirslope 62. In an embodiment, the nadirslope 62 may be determined by subtracting the minimum value 60 of the last desaturation pattern 38 from the minimum value 60 of the second to last desaturation pattern 38. In another embodiment, the nadirslope 62 may be determined using a linear regression on the minimum values 60 of all of the desaturation patterns 38 within the time period 48. Minimum values 60 from any number of the desaturation patterns 38 may be used for the determination of the nadirslope 62, depending on the sensitivity desired. In an embodiment, fewer desaturation patterns 38 may make the nadirslope 62 more sensitive to changes. In another embodiment, a histogram of nadir values over the time period 48 may be determined. The nadirslope 62 may then be calculated as the mean of the Nth highest nadirs minus the mean of Nth lowest nadirs in the histogram. In an embodiment N may be equal to 3. In other embodiments, N may be may be equal to 2, 4, 5, or any other number chosen by a practitioner to control the sensitivity of the nadirslope 62.

As shown in block 64 of FIG. 4, the method 50 may determine a maximum value for each desaturation pattern 38, as indicated by reference numeral 66 in FIG. 2. In an embodiment, the maximum value 66 may be the first point after the desaturation pattern 38 has ended. One of ordinary skill in the art will recognize that other points may be chosen for the maximum value 66. For example, the maximum value 66 may be the last point before a desaturation pattern 38 has started.

Once the maximum values 66 have been identified, a slope may be calculated from the maximum values 66, as shown in block 64 of FIG. 4. This slope may be termed the peakslope and is indicated by reference numeral 68 in FIG. 2. In an embodiment, the peakslope 68 may be determined by subtracting the maximum value 66 of the last desaturation pattern 38 from the maximum value 66 of the second to last desaturation pattern 38. In another embodiment, the peakslope 68 may be determined using a linear regression on the maximum values 66 from all of the desaturation patterns 38 within the time period 48. The maximum values 66 for any number of the desaturation patterns 38 may be used for the determination of the peakslope 68, depending on the sensitivity desired. In an embodiment, the use of fewer desaturation patterns 38 may make the peakslope 68 more sensitive to changes. In another embodiment, a histogram of nadir values over the time period 48 may be determined. The peakslope 68 may then be calculated as the mean of the Nth highest peaks minus the mean of Nth lowest peaks in the histogram. An embodiment may include N=3.

As shown in block 70 of FIG. 4, the method 50 may determine the absolute value of the change between the maximum and minimum values of the last desaturation pattern, indicated by reference numeral 72 on FIG. 2. This difference may be termed the magnitude 72. As noted for the minimum value 60 and maximum value 66, discussed above, The magnitude 72 of the change may be made using various points selected from the $SpO_2$ signal 34. In an embodiment, the magnitude 72 may be calculated by subtracting the minimum value 60 of a desaturation pattern 38 from the maximum value 66, where the maximum value 66 is the first point after the desaturation pattern 38 ends. In another embodiment, the SPDi equation may be equal to the average magnitude of all desaturation patterns within the measurement period.

The values calculated from the $SpO_2$ signal 34, as discussed above, may be used to calculate the SPDi. In an embodiment, this may be done by the formula given below:

$$\text{Saturation pattern detection index} = (\text{clusterweight}^* \\ (a^*\text{magnitude} + b^*\text{peakslope} + c^*\text{nadirslope})) + \\ d^*\text{duration}$$

In the equation set forth above, clusterweight is a factor used to weight the SPDi by the number of desaturation patterns 38 present in the time period 48. Referring again to FIG. 2, in an embodiment, if any clusters 46 are present in the time period 48, the clusterweight may be set to 3. The clusterweight may also be a function of cluster morphology. Unstable or erratic desaturation patterns may have a larger cluster weight than relatively stable patterns. Additional clinical research may show that one pattern shape is more dangerous than another and the cluster weight may be set accordingly.

If no clusters 46 are present, the clusterweight may be set to 1. The parameters "a," "b" and "c" are weighting factors that may be used to change the response of the SPDi to different factors in the $SpO_2$ signal 34 that may reflect different physiological conditions. In an embodiment, increasing "a" will increase the change of the SPDi in response to a change in the magnitude 72 of the last desaturation pattern 38. This may be useful, for example, if very deep desaturation patterns 38 are problematic for a particular patient. In an embodiment, changing "b" will change the response of the SPDi to the change in the level of the recovery after each desaturation pattern 38 has ended. This may be useful for alerting a practitioner if the recovery after the desaturation patterns 38 is generally decreasing, which may indicate a worsening condition. Similarly, changing "c" will affect the response of the SPDi to the change in the depth of each successive desaturation pattern 38. Referring again to FIG. 2, this factor may be useful for alerting practitioners if the desaturation patterns 38 are generally dropping to lower minimum values 60.

The final term in equation 1, d*duration, may be used to weight the SPDi based on a period of time that desaturation patterns are present. This period of time, termed "duration" may be measured as the number of consecutive seconds that desaturation patterns are present. The term "d" may be used to increase the weight of the duration, with higher values for d increasing contribution of the duration to the SPDi. One of ordinary skill in the art will recognize that other functions may be used to account for the time that desaturation patterns are present, depending on physiological considerations. In an embodiment, the duration may be set to zero if below a previously set threshold. In this case, the value of the SPDi would not be affected unless desaturation patterns were present for a certain period of time.

In some embodiments, the SPDi may be calculated based on identification of a certain number of clusters within a specified time period or window. Indeed, performing a calculation of the SPDi may be limited to when a certain number of clusters are present. The medical device 10 may be capable of performing an algorithm that maintains an internal reciprocation counter that keeps track of a number of qualified reciprocations that are currently present. When the reciprocation counter is greater than or equal to a certain value, such as 5, the clustering state may be set to "active" and the algorithm may begin calculating and reporting the SPDi. When clustering is not active (e.g., reciprocation count<5) the algorithm may not calculate the SPDi.

The medical device 10 may utilize various rules to determine the reciprocation count. For example, when the clustering state is inactive, the following rules may be observed:
1.) If the distance between qualified reciprocation exceeds 120 seconds, then the reciprocation count=0;
2.) If the current reciprocation is qualified, and the time from the start of the current reciprocation to the end of the last qualified reciprocation is <=120 seconds, then the reciprocation count=reciprocation count+1;
3.) If the current reciprocation is not qualified, then the reciprocation count=max(reciprocation count−2, 0).

Once clustering is active, it may remain active until the time between two qualified reciprocations exceeds 120 seconds. The following table (Table VIII) illustrates an example of how the reciprocation count rules may be applied to determine a clustering state.

TABLE VIII

| Current Reciprocation Qualified | Time Since Last Qualified Reciprocation (seconds) | Reciprocation Count | Clustering State |
|---|---|---|---|
| TRUE | N/A | 1 | INACTIVE |
| FALSE | 60 | 0 | INACTIVE |
| TRUE | N/A | 1 | INACTIVE |
| FALSE | 60 | 0 | INACTIVE |
| TRUE | N/A | 1 | INACTIVE |
| TRUE | 30 | 2 | INACTIVE |
| TRUE | 120 | 3 | INACTIVE |
| FALSE | 60 | 1 | INACTIVE |
| TRUE | 10 | 2 | INACTIVE |

TABLE VIII-continued

| Current Reciprocation Qualified | Time Since Last Qualified Reciprocation (seconds) | Reciprocation Count | Clustering State |
|---|---|---|---|
| TRUE | 20 | 3 | INACTIVE |
| TRUE | 40 | 4 | INACTIVE |
| FALSE | 30 | 2 | INACTIVE |
| FALSE | 60 | 0 | INACTIVE |
| TRUE | N/A | 1 | INACTIVE |
| TRUE | 20 | 2 | INACTIVE |
| TRUE | 120 | 3 | INACTIVE |
| TRUE | 10 | 4 | INACTIVE |
| FALSE | 90 | 2 | INACTIVE |
| TRUE | 120 | 3 | INACTIVE |
| TRUE | 60 | 4 | INACTIVE |
| TRUE | 20 | 5 | ACTIVE |
| TRUE | 30 | 6 | ACTIVE |
| FALSE | 50 | 6 | ACTIVE |
| FALSE | 100 | 6 | ACTIVE |
| TRUE | 121 | 1 | INACTIVE |
| FALSE | 50 | 0 | INACTIVE |
| TRUE | N/A | 1 | INACTIVE |
| TRUE | 30 | 2 | INACTIVE |
| TRUE | 121 | 1 | INACTIVE |
| TRUE | 10 | 2 | INACTIVE |
| TRUE | 20 | 3 | INACTIVE |
| TRUE | 40 | 4 | INACTIVE |
| TRUE | 40 | 5 | ACTIVE |

When the clustering state is active, an unfiltered SPDi may be calculated for each new qualified reciprocation. The following formula may be used by the medical device 10 to calculate the SPDi:

$$\text{Unfiltered SPDi} = a * \text{Magnitude} + b * \text{PeakDelta} + c * \text{NadirDelta};$$

wherein a=1.4, b=2.0, c=0.2;
wherein Magnitude=average magnitude of all reciprocations in the last 6 minutes;
wherein PeakDelta=average of the three highest qualified reciprocation rise peaks in the last 6 minutes minus the average of the three lowest qualified reciprocation rise peaks in the last 6 minutes; and
wherein NadirDelta=average of the three highest qualified reciprocation nadirs in the last 6 minutes minus the average of the three lowest qualified reciprocation nadirs in the last 6 minutes.
Wherein SPDi<=31.

The above formula may be utilized to quantify the severity of a ventilatory instability pattern. The constants and metrics used may vary and may be based on input from clinical team members. It should be noted that the PeakDelta parameter may be assigned the largest weighting constant since the most severe patterns generally have peak reciprocation values that do not recover to the same baseline.

The unfiltered SPDi may be updated whenever clustering is active and a new qualified reciprocation is detected. Non-zero SPDi values may be latched for a period of time (e.g., 6 minutes). The unfiltered SPDi may then be low pass filtered to produce the final output SPDi value. The following IIR filter with a response time of approximately 40 seconds may be used:

$$\text{SPDi} = \text{Unfiltered SPDi}/a + \text{Previous Filtered SPDi} * (a-1)/a;$$

wherein a=40.

Figure 5:
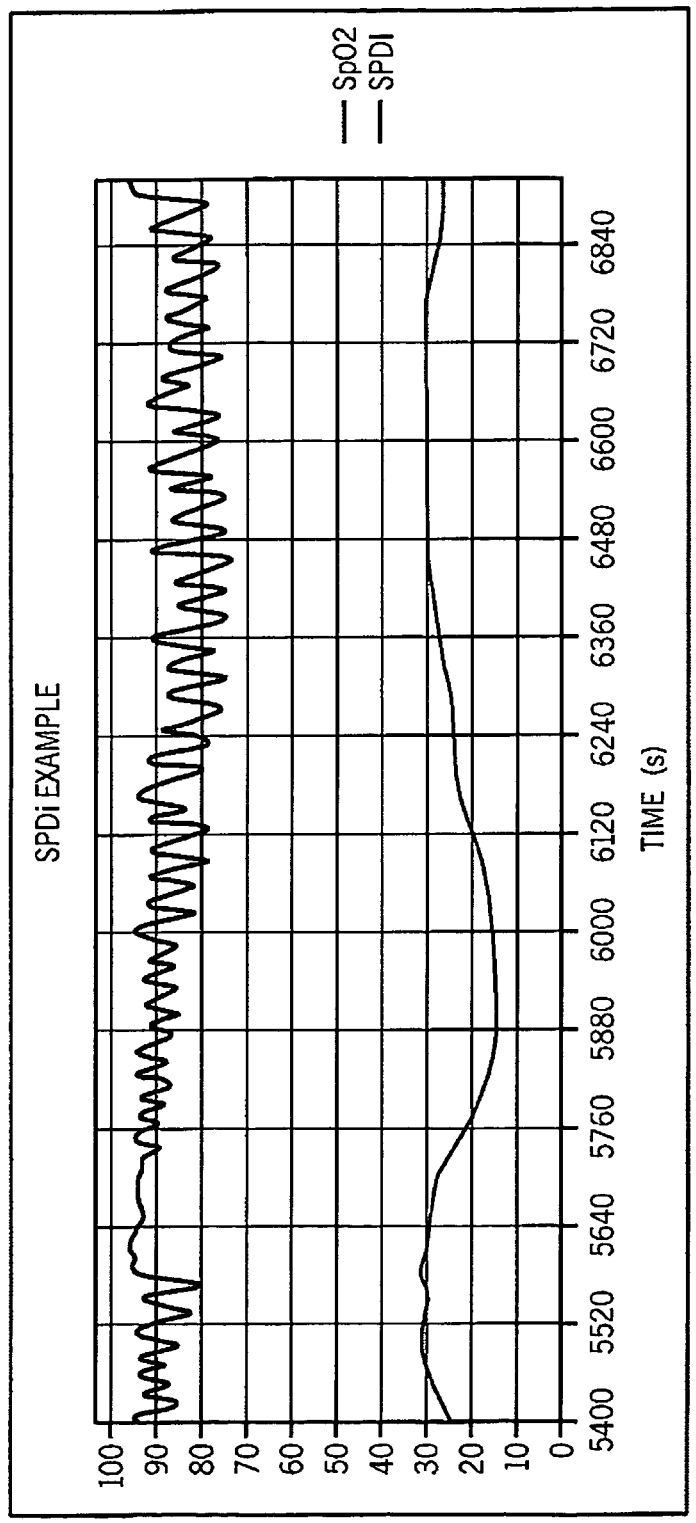
FIG. 5 is an exemplary graph including an $SpO_2$ trend that contains a ventilatory instability $SpO_2$ pattern and a trend of the resulting index in accordance with various embodiments.

FIG. 5 is an exemplary graph including an $SpO_2$ trend that contains a ventilatory instability $SpO_2$ pattern and a trend of the resulting SPDi. In the illustrated example, it should be noted that the SPDi is sensitive to the decreasing peaks (incomplete recoveries) starting at approximately t=6000.

After the SPDi is calculated, it may be reported to a practitioner, as shown in block 76 of FIG. 4. In addition to being reported, the value of the SPDi may be used to activate or deactivate a treatment device 30 or an audio recording device 32, as discussed with respect to FIG. 1. Further, in an embodiment, alarm signals, either on the medical device 10 or on a device connected to the local area network 28 may be activated based on the value of the SPDi. After the SPDi is reported, the method 50 may return to block 52 to continue.

The operation of an embodiment of the method 50 discussed with respect to FIG. 4, may be illustrated by the charts shown in FIGS. 6-10. In each of these charts, as in FIG. 2, the $SpO_2$ signal 34 is plotted against the % blood oxygen saturation level ($SpO_2$) on the left vertical axis 36 and the time in seconds on the horizontal axis 38. The horizontal line at a value of 85% for $SpO_2$, indicated by reference numeral 36, represents an absolute setpoint 78 that may be used by the practitioner for controlling alarms. The SPDi 80 is plotted on each chart, showing the response of the method 50 under the conditions described.

Figure 6:
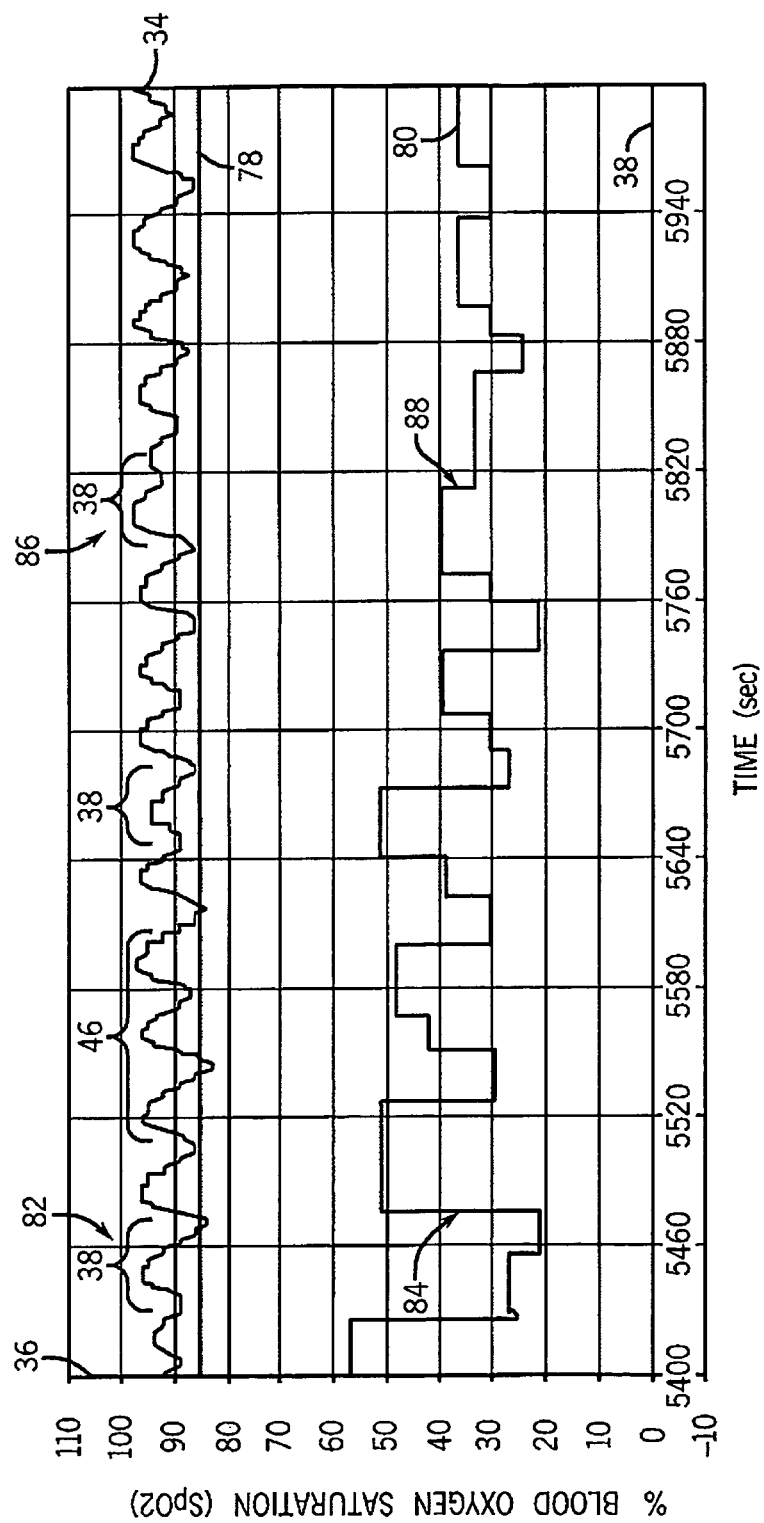
FIG. 6 is a chart of $SpO_2$ data which may be useful to demonstrate the response of a calculated index, in accordance with various embodiments.

FIG. 6 is a chart that may illustrate the performance of the method 50 during a period of relative stability in the $SpO_2$ signal 34, according to an embodiment. As can be seen from the chart, the stability of the SPDi 80 reflects the relative stability of the $SpO_2$ signal 34. However, the presence of desaturation patterns 38 and clusters 46 is reflected in the SPDi 80, which is significantly above the baseline. It may also be noted that deeper desaturation patterns 38, as indicated by reference numeral 82 may lead to large changes in the SPDi 80, as indicated by reference numeral 84. Similarly, shallower desaturation patterns 38, as indicated by reference numeral 86, may lead to decreases in the SPDi 80, as indicated by reference numeral 88.

Figure 7:
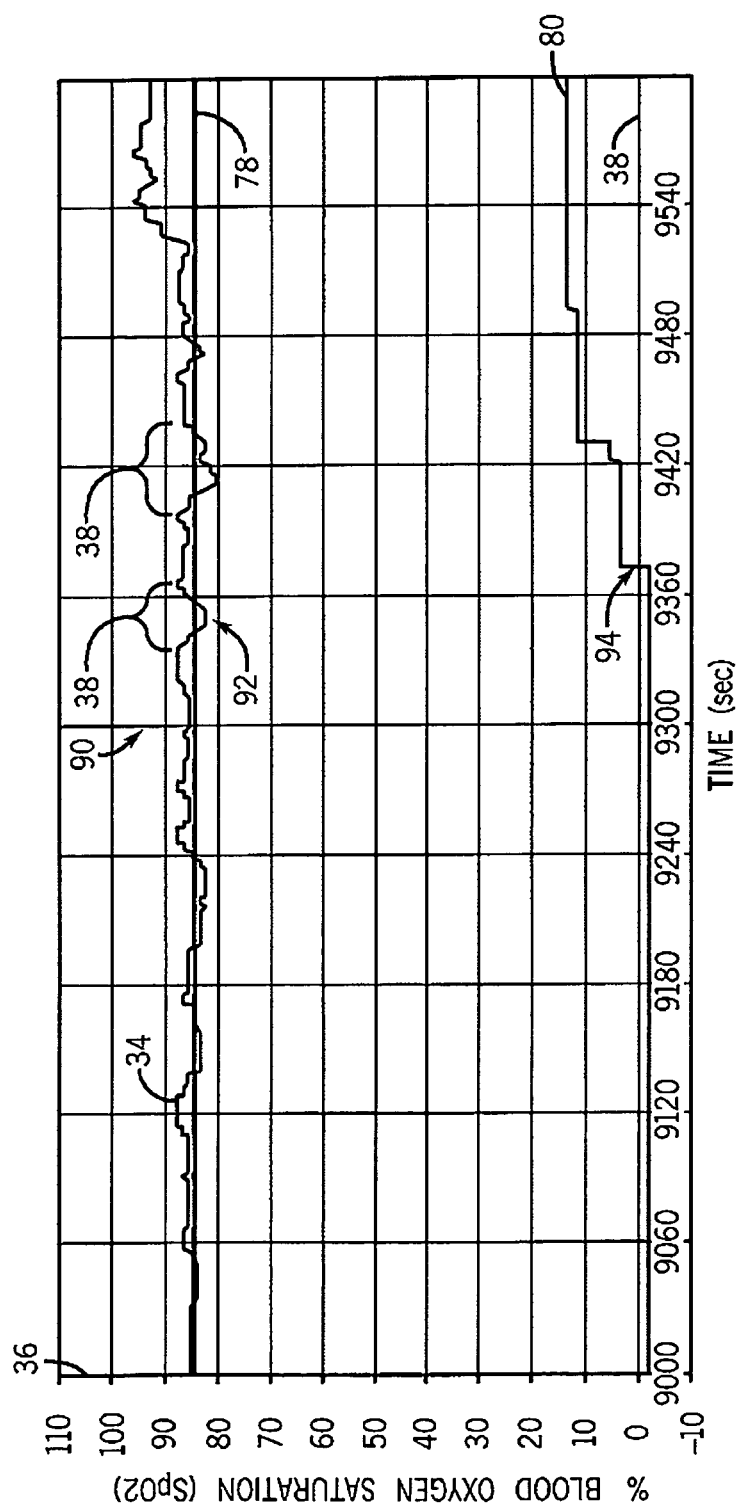
FIG. 7 is a chart of $SpO_2$ data which may be useful to demonstrate the response of a calculated index, in accordance with various embodiments.

FIG. 7 is a chart that may illustrate the performance of the method 50 when no desaturation patterns 38 are present in the $SpO_2$ signal 34. Although the $SpO_2$ signal is close to the 85% saturation level, no desaturation patterns 38 are present in the signal 34 prior to around 9300 seconds on this chart, indicated by reference numeral 90. However, an initial desaturation pattern 38 appears in the signal around 9340 seconds, as indicated by reference numeral 92, resulting in a non-zero value for the SPDi 80, as indicated by reference numeral 94. From this point on, desaturation patterns 38 are continuing to occur in the signal 34, which results in the method 50 calculating non-zero values for the SPDi 80.

Figure 8:
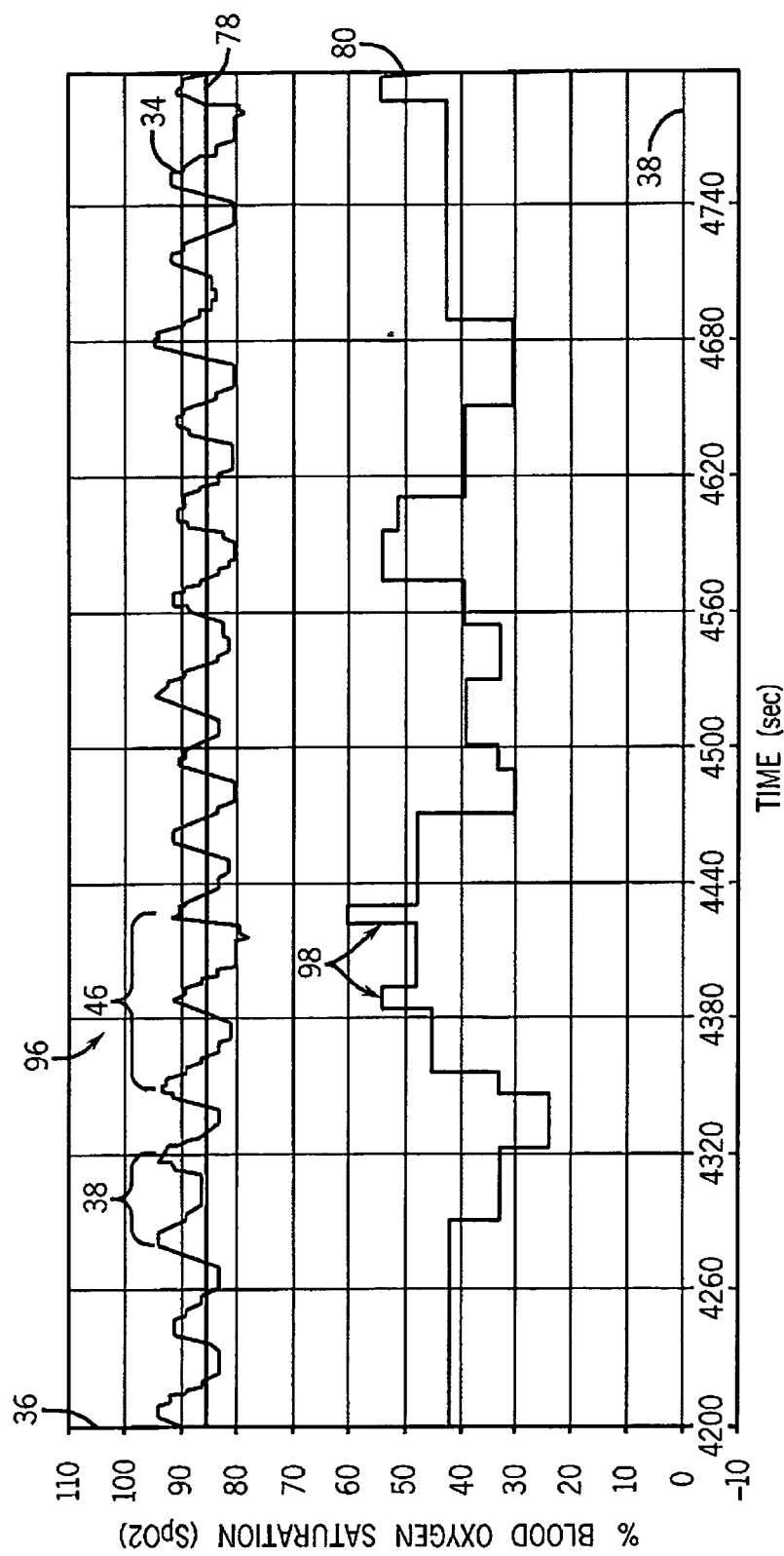
FIG. 8 is a chart of SpO$_2$ data which may be useful to demonstrate the response of a calculated index, in accordance with various embodiments.
Figure 9:
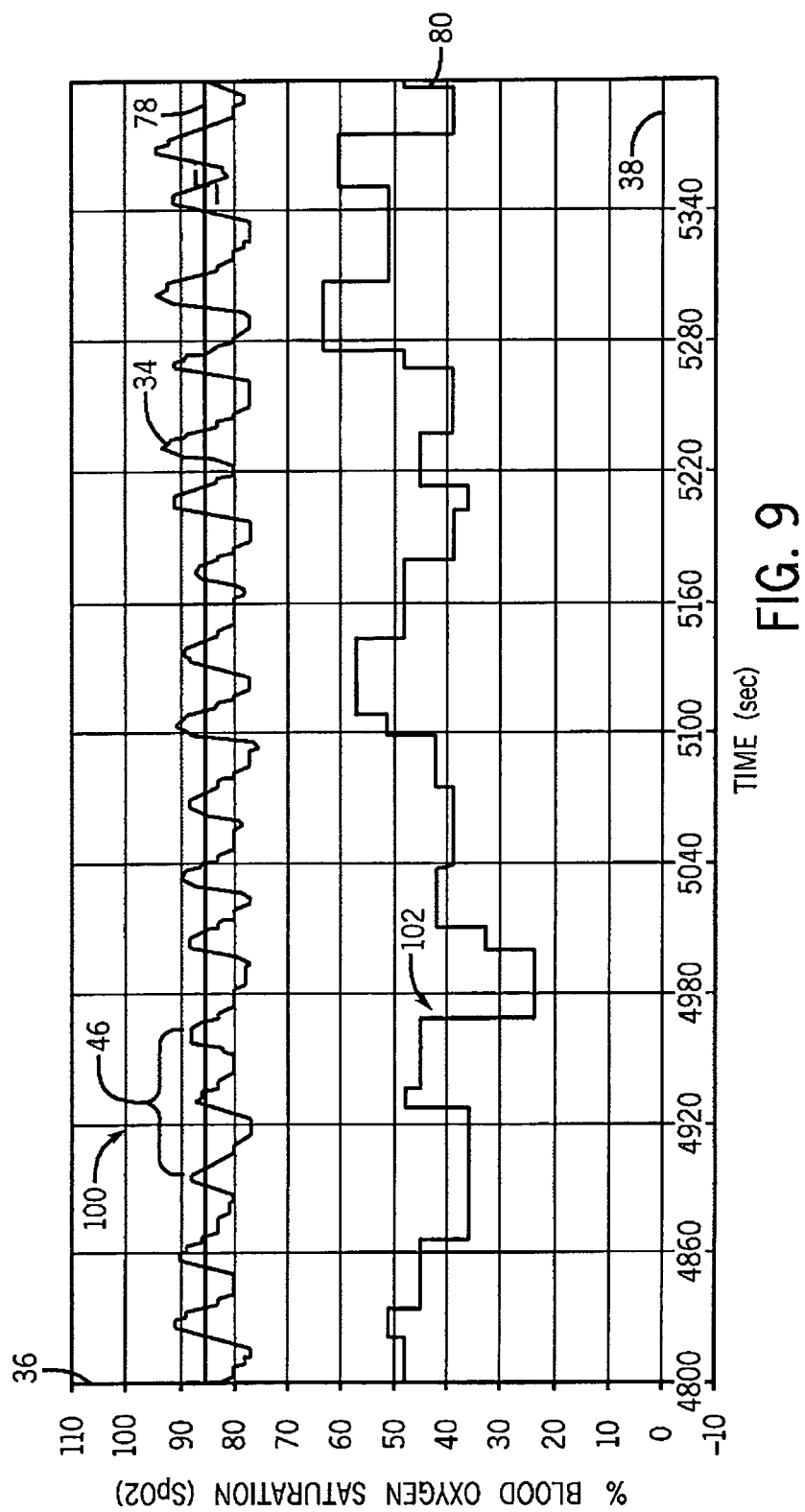
FIG. 9 is a chart of SpO$_2$ data which may be useful to demonstrate the response of a calculated index, in accordance with various embodiments.

FIGS. 8 and 9 are charts that may illustrate the usefulness of the method 50 for analyzing the breathing patterns of a patient. For example, while the absolute value of the $SpO_2$ signal 34 may be lower in FIG. 9 than in FIG. 8, as illustrated by the larger amount of the signal that is below the 85% setpoint 78, the value of the SPDi 80 calculated may not be significantly different. However, particular types of desaturation patterns 38 will lead to increases in the value of the SPDi 80. For example, in FIG. 8, a cluster 46 in which the desaturation patterns 38 are continuously deepening, indicated by reference numeral 96, may lead to substantial increases in the SPDi 80, as indicated by reference numeral 98. Similarly, in FIG. 9, a cluster 46 in which the patterns are growing more shallow, as indicated by reference numeral 100, leads to a drop in the value of the SPDi 80, as indicated by reference numeral 102.

The SPDi 80 may be used in conjunction with absolute alarms to alert a practitioner to a physiological condition. In an embodiment, an alarm may be activated when the SPDi 80 reaches a previously selected level, and the $SpO_2$ signal remains below setpoint 78 for a selected period of time. Selection of alarming values for the setpoint 78 and the SPDi 80 may depend on the particular patient and condition involved.

Figure 10:
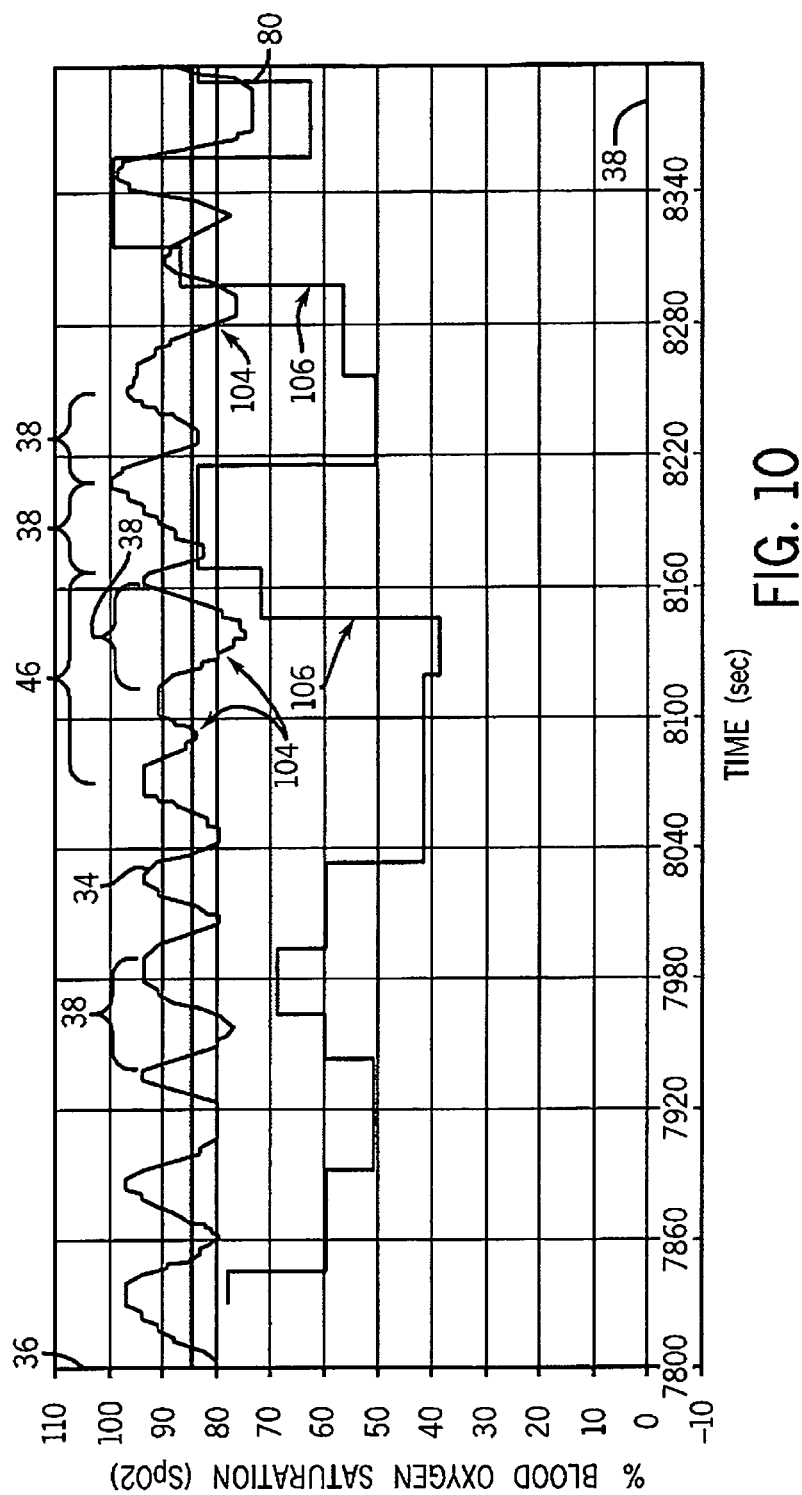
FIG. 10 is a chart of SpO$_2$ data which may be useful to demonstrate the response of a calculated index, in accordance with various embodiments.

FIG. 10 is a chart that may illustrate the usefulness of the method 50 in identifying particularly unstable periods of desaturation patterns 38. As shown in this chart, the instability of the signal 34, as shown by significant variations in the depths and shapes of the desaturation patterns 38, causes the value of the SPDi 80 to be relatively higher than seen for more regular patterns, for example, those shown in FIGS. 8 and 9. Further, this chart may illustrate that multiple significant decreases in desaturation patterns 38, as indicated by reference numeral 104, may result in large increases in the SPDi 80, as indicated by reference numeral 106.

While the disclosure described above may be susceptible to various modifications and alternative forms, various embodiments have been shown by way of example in the drawings and have been described in detail herein. However, it should be understood that the disclosure is not intended to be limited to the embodiments for calculating SPDi presented herein. Rather, the disclosure is to cover all modifications, equivalents, and alternatives falling within the spirit and scope of the disclosure as defined by the following appended claims.

What is claimed is:

1. A method of evaluating a physiological parameter, comprising:
   monitoring a patient with a monitor to produce physiological parameter data comprising a sequence indicative of blood oxygen saturation over a time period;
   analyzing the physiological parameter data with a processor to identify at least a first desaturation pattern and a second desaturation pattern within the time period;
   determining a first maximum value of the first desaturation pattern and a second maximum value of the second desaturation pattern with the processor;
   calculating a peak slope between the first and second maximum values with the processor;
   calculating a saturation pattern detection index based at least in part upon the peak slope with the processor; and
   providing an indication of sleep apnea based at least in part upon the saturation pattern detection index.

2. The method of claim 1, comprising calculating the saturation pattern detection index based at least in part upon a nadir slope between minimum values of the physiological parameter data during each of the first and second desaturation patterns.

3. The method of claim 1, comprising using the processor to incrementally scale the saturation pattern detection index based at least in part upon a count of the desaturation patterns present within the time period.

4. The method of claim 1, comprising using the processor to incrementally scale the saturation pattern detection index based at least in part upon a duration of time during which desaturation patterns are present.

5. A medical system, comprising:
   a microprocessor configured to process physiological parameter data representative of blood oxygen saturation; and
   a memory storing computer-readable instructions, that when executed direct the microprocessor to:
   analyze the physiological parameter data to identify at least a first desaturation pattern and a second desaturation pattern within the time period;
   determine a first maximum value of the first desaturation pattern and a second maximum value of the second desaturation pattern;

calculate a peak slope between the first and second maximum values;

calculate a saturation pattern detection index based at least in part upon the peak slope; and provide an indication of sleep apnea based at least in part upon the saturation pattern detection index.

6. The medical system of claim 5, wherein the computer-readable instructions, if executed by the microprocessor, cause the microprocessor to calculate the saturation pattern detection index based at least in part upon a nadir slope between minimum values of the physiological parameter data during each of the first and second desaturation patterns.

7. The medical system of claim 5, wherein the computer-readable instructions, when executed by the microprocessor, are configured to cause the microprocessor to calculate a magnitude comprising the difference between a maximum value of the physiological parameter data during a last desaturation pattern within the time period and a minimum value of the physiological parameter data of the last desaturation pattern within the time period.

8. The medical system of claim 5, wherein the computer-readable instructions, when executed by the microprocessor, are configured to cause the microprocessor to scale the saturation pattern detection index based at least in part upon a count of the desaturation patterns present within the time period.

9. The medical system of claim 5, wherein the computer-readable instructions, if executed by the microprocessor, are configured to cause the microprocessor to scale the saturation pattern detection index based at least in part upon a duration of time over which desaturation patterns are occurring.

10. A tangible, non-transitory computer readable medium, comprising computer readable code that when executed by a computer is configured to:

obtain physiological parameter data from a measurement device monitoring a patient, wherein the physiological parameter data comprises an indication of blood oxygen saturation over a time period;

analyze the physiological parameter data to identify at least a first desaturation pattern and a second desaturation pattern within the time period;

determine a first maximum value of the first desaturation pattern and a second maximum value of the second desaturation pattern;

calculate a peak slope between the first and second maximum values;

calculate a saturation pattern detection index based at least in part upon the peak slope; and provide an indication of sleep apnea based at least in part upon the saturation pattern detection index.

11. The tangible, non-transitory computer readable medium of claim 10, comprising computer readable code that when executed is configured to calculate the saturation pattern detection index based at least in part upon a nadir slope between minimum values of the physiological parameter data during each of the first and second desaturation patterns.

12. The tangible, non-transitory computer readable medium of claim 10, comprising computer readable code that when executed is configured to calculate a magnitude comprising the difference between a maximum value of the oxygen saturation of a last desaturation pattern within the time period and a minimum value of the oxygen saturation of the last desaturation pattern within the time period.

13. The tangible, non-transitory computer readable medium of claim 10, comprising computer readable code that when executed is configured to incrementally scale the saturation pattern detection index based at least in part upon a count of the desaturation patterns present within the time period.

14. The tangible, non-transitory computer readable medium of claim 10, comprising computer readable code that when executed is configured to increase the saturation pattern detection index based at least in part upon a duration of time over which desaturation patterns are present.

15. The tangible, non-transitory computer readable medium of claim 10, comprising computer readable code that when executed is configured to control a treatment device based at least in part upon the saturation pattern detection index.

16. The tangible, non-transitory computer readable medium of claim 10, comprising computer readable code that when executed is configured to control an audio recording device based at least in part upon the saturation pattern detection index.

* * * * *